United States Patent [19]

Akhavan-Tafti et al.

[11] Patent Number: 5,721,370

[45] Date of Patent: Feb. 24, 1998

[54] WATER SOLUBLE TRI-SUBSTITUTED 1,2-DIOXETANE COMPOUNDS AND ASSAY COMPOSITIONS HAVING INCREASED STORAGE STABILITY

[75] Inventors: Hashem Akhavan-Tafti; Zahra Arghavani, both of Brighton; Renuka DeSilva, Northville; Kumar Thakur, Southfield, all of Mich.

[73] Assignee: Lumigen Inc., Southfield, Mich.

[21] Appl. No.: 748,107

[22] Filed: Nov. 8, 1996

Related U.S. Application Data

[63] Continuation-in-part of Ser. No. 509,305, Jul. 31, 1995.

[51] Int. Cl.$^6$ .............................. C07F 9/28; C07D 321/00
[52] U.S. Cl. .................... 549/218; 549/214; 549/332; 549/510
[58] Field of Search ..................... 549/214, 218, 549/332, 510

[56] References Cited

U.S. PATENT DOCUMENTS

| | | | |
|---|---|---|---|
| 4,952,707 | 8/1990 | Edwards | 549/221 |
| 4,959,182 | 9/1990 | Schaap | 252/700 |
| 5,004,565 | 4/1991 | Schaap | 252/700 |
| 5,013,827 | 5/1991 | Schaap | 536/4.1 |
| 5,068,339 | 11/1991 | Schaap | 548/110 |
| 5,112,960 | 5/1992 | Bronstein | 536/18.1 |
| 5,145,772 | 9/1992 | Voyta | 435/4 |
| 5,220,005 | 6/1993 | Bronstein | 549/221 |
| 5,393,469 | 2/1995 | Akhavan-Tafti | 252/700 |
| 5,399,497 | 3/1995 | Kumar | 436/53 |

FOREIGN PATENT DOCUMENTS

| | | |
|---|---|---|
| 0473984 | 3/1992 | European Pat. Off. . |
| 0630884 | 12/1994 | European Pat. Off. . |
| 8800695 | 1/1988 | WIPO . |
| 9410258 | 5/1994 | WIPO . |
| 9421821 | 9/1994 | WIPO . |
| 9426726 | 11/1994 | WIPO . |

OTHER PUBLICATIONS

Schaap, A.P., et al., Tetrahedron Lett., 28(9), 935-8 (1987).
Schaap, A.P., et al., Tetrahedron Lett., 28(11), 1159-62 (1987).
Schaap, A.P., Photochem. Photobiol., 47S, 50S (1988).
Schaap, A.P., Clinical Chemistry, 35(9), 1853-4 (1989).
Martin Josso, Ph.D. Thesis, Wayne State Univ. (1992), Diss. Abs. Int., vol. 53, No. 12B, p. 6305.

*Primary Examiner*—Amelia A. Owens
*Attorney, Agent, or Firm*—Richard S. Handley

[57] ABSTRACT

Stable, enzymatically triggered chemiluminescent 1,2-dioxetanes with improved water solubility and storage stability are provided. Dioxetanes further substituted with two or more water-solubilizing groups disposed on the dioxetane structure and an additional fluorine atom or lower alkyl group provide superior performance by eliminating the problem of reagent carryover when used in assays performed on capsule chemistry analytical systems. These dioxetanes display substantially improved stability on storage. Compositions comprising these dioxetanes, a non-polymeric cationic surfactant enhancer and optionally a fluorescer, for providing enhanced chemiluminescence are also provided.

6 Claims, 5 Drawing Sheets

WATER SOLUBLE TRI-SUBSTITUTED 1,2-DIOXETANE COMPOUNDS AND ASSAY COMPOSITIONS HAVING INCREASED STORAGE STABILITY

CROSS REFERENCE TO RELATED APPLICATION

This application is a continuation-in-part of applicants' co-pending U.S. Application Ser. No. 08/509,305 filed on Jul. 31, 1995.

BACKGROUND OF THE INVENTION

(1) Field of the Invention

The present invention relates to stable 1,2-dioxetanes and compositions which can be triggered by chemical reagents, including enzymes, to generate chemiluminescence. The dioxetanes contain more than one ionizable group which are part of an alkoxy substituent. The dioxetanes further contain a fluorine atom or lower alkyl group substituted for one of the hydrogen atoms on the alkoxy substituent which improve the storage stability of the dioxetane. Compositions used in the practice of the invention contain a stable dioxetane as described above, a cationic surfactant and optionally a fluorescer which enhance the amount of chemiluminescence which is produced. Dioxetanes and enhanced compositions of the present invention are useful in methods for generating light (chemiluminescence) and in methods of analysis for detecting the presence or amount of an analyte. Importantly, the ionizable groups afford a more water soluble dioxetane and solve an unexpected chemical carry-over problem in capsule chemistry analytical systems, while the presence of the fluorine atom or lower alkyl group improves the storage stability of the dioxetane.

(2) Description of Related Art a. Enzymatically Triggerable Dioxetanes

The first examples of enzymatic triggering of dioxetanes are described in a U.S. patent application (A. P. Schaap, U.S. patent application Ser. No. 887,139) and a series of papers (A. P. Schaap, R. S. Handley, and B. P. Giri, *Tetrahedron Lett.*, 935 (1987); A. P. Schaap, M. D. Sandison, and R. S. Handley, *Tetrahedron Lett.*, 1159 (1987) and A. P. Schaap, *Photochem. Photobiol.*, 47S, 50S (1988)). The highly stable adamantyl-substituted dioxetanes bearing a protected aryloxide substituent are triggered to decompose with emission of light by the action of both an enzyme and aqueous buffer to give a strongly electron-donating aryloxide anion which dramatically increases the rate of decomposition of the dioxetane. As a result, chemiluminescence is emitted at intensities several orders of magnitude above that resulting from slow thermal decomposition of the protected form of the dioxetane. U.S. Pat. No. 5,068,339 to Schaap discloses enzymatically triggerable dioxetanes with covalently linked fluorescer groups decomposition of which results in enhanced chemiluminescence via energy transfer to the fluorescer. U.S. Pat. Nos. 5,112,960 and 5,220,005 and a PCT application (WO88/00695) to Bronstein disclose triggerable dioxetanes bearing substituted adamantyl groups. U.S. Pat. No. 4,952,707 to Edwards discloses phosphate-substituted dioxetanes. A PCT application (WO94/26726) to Bronstein discloses adamantyl dioxetanes bearing a phenyl or naphthyl group substituted at a non-conjugated position with an enzyme labile OX group and with an additional group on the aryl ring.

Other triggerable dioxetanes are disclosed in a PCT application (WO94/10258) to Wang. The dioxetanes disclosed in Wang contain an alkoxy group which may be mono-substituted and a substituted phenyl-OX group wherein one or more non-hydrogen groups are present on the benzene ring substituent in addition to the triggerable OX group.

Dioxetanes disclosed in all of the foregoing publications generate a light-emitting carbonyl compound comprising an alkyl ester of an aromatic carboxylic acid, typically the methyl ester of a hydroxybenzoic or hydroxynaphthoic acid or else a hydroxyaryl ketone.

Applicants' co-pending U.S. Application Ser. No. 08/509,305 ('305 application) filed on Jul. 31, 1995 discloses disubstituted dioxetanes whose hydroxy dioxetane shows improved water solubility and is fully incorporated herein by reference.

b. Surfactant Enhancement of Chemiluminescence from Triggerable Dioxetanes

Enhancement of chemiluminescence from the enzyme-triggered decomposition of a stable 1,2-dioxetane in the presence of water-soluble substances including an ammonium surfactant and a fluorescer has been reported (A. P. Schaap, H. Akhavan and L. J. Romano, Clin. Chem., 35(9), 1863 (1989)). Fluorescent micelles consisting of cetyltrimethylammonium bromide (CTAB) and 5-(N-tetradecanoyl) amino-fluorescein capture the intermediate hydroxy-substituted dioxetane and lead to a 400-fold increase in the chemiluminescence quantum yield by virtue of an efficient transfer of energy from the anionic form of the excited state ester to the fluorescein compound within the hydrophobic environment of the micelle.

U.S. Pat. Nos. 4,959,182 and 5,004,565 to Schaap describe additional examples of enhancement of chemiluminescence from chemical and enzymatic triggering of stable dioxetanes in the presence of micelles formed by the quaternary ammonium surfactant CTAB. Fluorescent micelles also enhance light emission from the base-triggered decomposition of hydroxy- and acetoxy-substituted dioxetanes.

U.S. Pat. No. 5,145,772 to Voyta discloses enhancement of enzymatically generated chemiluminescence from 1,2-dioxetanes in the presence of polymers with pendant quaternary ammonium groups alone or admixed with fluorescein. Other substances reported to enhance chemiluminescence include globular proteins such as bovine albumin and quaternary ammonium surfactants. Other cationic polymer compounds were marginally effective as chemiluminescence enhancers; nonionic polymeric compounds were generally ineffective and an anionic polymer significantly decreased light emission. A PCT application (WO 94/21821) to Bronstein describes the use of mixtures of the aforementioned polymeric quaternary ammonium surfactant enhancers with enhancement additives.

The enhancement and catalysis of a non-triggerable dioxetane by pyranine in the presence of CTAB is described (Martin Josso, Ph.D. Thesis, Wayne State University (1992), Diss. Abs. Int., Vol. 53, No. 12B, p. 6305).

U.S. Pat. No. 5,393,469 to Akhavan-Tafti discloses enhancement of enzymatically generated chemiluminescence from 1,2-dioxetanes in the presence of polymeric quaternary phosphonium salts optionally substituted with fluorescent energy acceptors.

European Patent Application Serial No. 94108100.2 discloses enhancement of enzymatically generated chemiluminescence from 1,2-dioxetanes in the presence of dicationic phosphonium salts. No documents disclose the combination of an anionic fluorescer and a dicationic enhancer for enhancing chemiluminescence from a triggerable dioxetane. No example of enhancement of substituted dioxetanes of the type of the present invention has been reported.

c. Triggerable Dioxetanes with Improved Water Solubility

The enzymatically triggerable dioxetanes are now undergoing widespread use as substrates for marker enzymes in numerous applications including immunoassays, gene expression studies, Western blotting, Southern blotting, DNA sequencing and the identification of nucleic acid segments in infectious agents. Despite the growing use of these compounds, there are limitations to there use in some assay methods. Triggerable dioxetanes whose hydroxy dioxetane deprotected form are more water-soluble are desirable. As shown in the structures below, it is especially desirable that the hydroxy dioxetane formed by the dephosphorylation of a phosphate dioxetane by alkaline phosphatase be highly soluble in aqueous solutions and in compositions containing chemiluminescence enhancing substances. Such dioxetanes and compositions are of importance in certain solution assay methods for detecting hydrolytic enzymes or conjugates of hydrolytic enzymes.

groups which interfere with the removal of the protecting group which initiates light emission or which otherwise interfere with light production would be of no value. Solubilizing groups which would be removed during the luminescent reaction likewise would not be useful.

In Applicant's co-pending '305 application it was demonstrated that incorporation of one ionic solubilizing group was insufficient to eliminate the carryover problem associated with the hydroxy dioxetane produced by dephosphorylation of a phosphate dioxetane. Phosphate dioxetanes whose hydroxy dioxetane product is highly water soluble and enhanced compositions containing such phosphate dioxetanes were provided to solve this problem. It was subsequently discovered that dioxetanes which provided the solution to the carryover problem, exhibited insufficient storage stability at room temperature. Thus, no dioxetanes known in the art possessed both high solubility of the hydroxy dioxetane and long term storage stability.

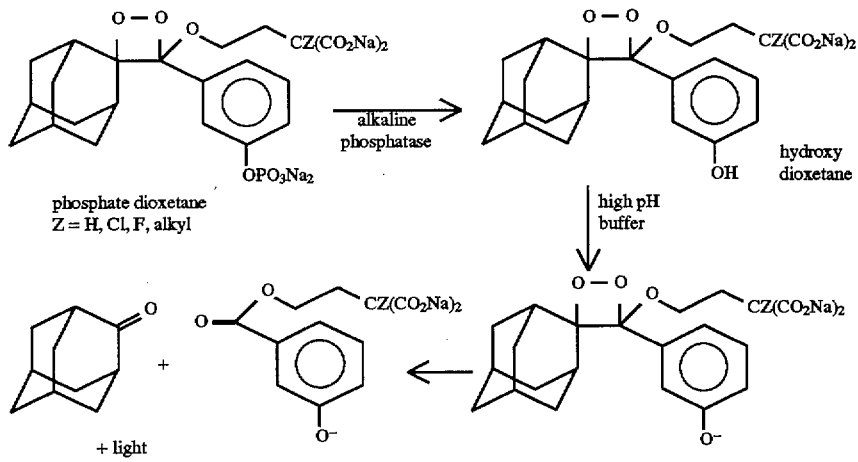

As further background of the present invention and as more fully explained in the examples below, it has been found that use of conventional chemiluminescent dioxetane reagents in assays performed on automated instrumentation based on the principles of capsule chemistry analysis results in carryover of reagent from one fluid segment to another, resulting in potentially inaccurate measurements, erroneous results, and imprecision due to non-reproducibility. Capsule chemistry analysis is described in U.S. Pat. No. 5,399,497, which is fully incorporated by reference herein. It has been postulated that, among other possible means for overcoming the carryover problem, improved water solubility of the hydroxy dioxetane, in particular, might eliminate or minimize carryover of this luminescent reaction intermediate into adjacent fluid segments of a capsule chemistry analysis system.

Dioxetane compounds in commercial use do not incorporate any solubilizing groups which are appended to an alkoxy group. As such, these dioxetanes are unsuitable for use in assay methods requiring zero carryover. A suggestion of incorporating a solubilizing group into a dioxetane has been made (U.S. Pat. No. 5,220,005). A dioxetane with a carboxyl group substituted on an adamantyl substituent is claimed, however, the preparation of such a dioxetane is not described. Significantly, there is no disclosure of what effect the addition of a carboxyl group had, if any, on solubility and other properties of the dioxetane. There is no teaching in the art of how many solubilizing groups are required or what particular advantage might be conferred. Use of solubilizing It has now been further discovered that substitution of a hydrogen atom on the alkoxy group bearing two ionic solubilizing groups with a fluorine atom or lower alkyl group dramatically improves the storage stability of these dioxetanes.

OBJECTS

It is an object of the present invention to provide enzymatically triggered 1,2-dioxetanes with improved storage stability whose hydroxy dioxetane product formed upon action of a triggering enzyme is highly soluble in aqueous solution. It is a second object of the present invention to provide 1,2-dioxetanes substituted with two or more water-solubilizing ionic groups and either a fluorine atom or lower alkyl group disposed on an alkoxy substituent of the dioxetane structure which provide superior storage stability. It is a further object of the present invention to provide a composition comprising a fluorine or lower alkyl group-substituted dioxetane with two or more ionic water-solubilizing groups, a non-polymeric cationic enhancer and optionally a fluorescer, for providing enhanced chemiluminescence. It is a further object of the present invention to provide dioxetanes and compositions which, when used in assays performed on capsule chemistry analytical systems, eliminate the problem of reagent carryover and have extended storage stability.

IN THE DRAWINGS

DESCRIPTION OF THE PREFERRED EMBODIMENTS

Figure 1:
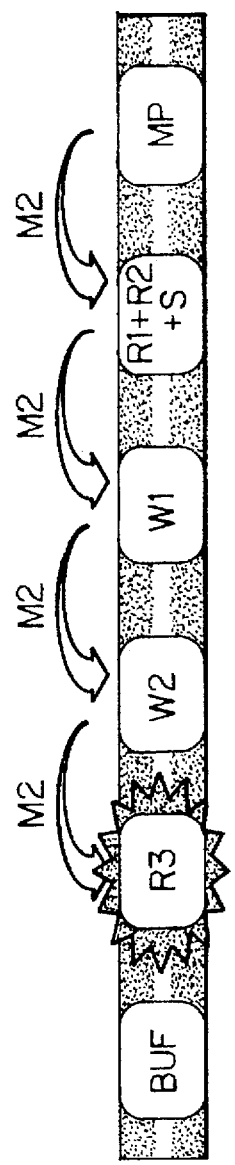
FIG. 1 is a diagram of a capsule chemistry analysis system in which carryover was determined to be a problem.

The present invention relates to dioxetanes with improved storage stability and whose hydroxy dioxetane product formed upon action of a triggering enzyme is highly soluble in aqueous solution and which are triggerable by an enzyme to produce chemiluminescence. Such triggerable dioxetanes eliminate or minimize carryover of the luminescent hydroxy dioxetane into adjacent segments in capsule chemistry analytical systems as described in U.S. Pat. No. 5,399,497. Carryover can result from solubilization, deposition or precipitation of light-emitting material of low water solubility into the fluorocarbon oil which serves as the isolating fluid in capsule chemistry systems. Reagent carryover can lead to inaccurate measurements, erroneous results and imprecision due to irreproducibility.

In the co-pending '305 application it was discovered that dioxetane 1 below was particularly effective for the chemiluminescent detection of alkaline phosphatase in aqueous solution.

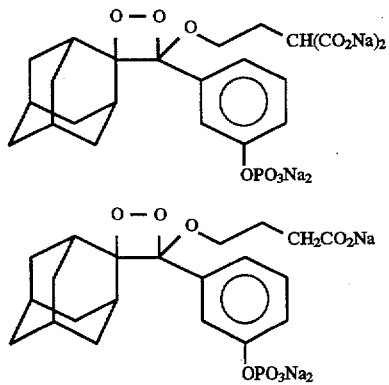

For comparison, dioxetane 2 which incorporates only one ionizable group was prepared. This dioxetane did not eliminate the carryover problem discussed above.

Use of dioxetane 1 in the test system described in U.S. Pat. No. 5,399,497 led to complete elimination of the carryover problem. However, it was subsequently discovered unexpectedly, that solutions of dioxetane 1 in aqueous buffer displayed unsatisfactory storage stability. Solutions containing 1 in alkaline buffer displayed significant decomposition after storage at 25° C. for two weeks. Dioxetane 1, in fact, was found to be significantly less stable than a related compound, Lumigen PPD, shown below which has no ionic solubilizing groups on the alkoxy group.

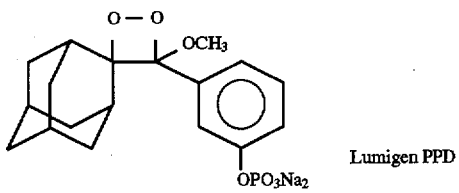

As far as Applicants are aware, there is no teaching in the art of dioxetane chemistry of the cause of the lower stability of 1 nor of means of structurally modifying 1 to improve its storage stability while preserving its other beneficial properties.

Definitions

Storage stability is related to the rate of decomposition of the dioxetane due to spontaneous reaction and is an intrinsic property. Decomposition of triggerable dioxetanes can also be induced by the presence of trace quantities of agents which catalyze the removal of a protecting group and thus initiate the decomposition. Storage stability of a dioxetane can be assessed by measuring the quantity of dioxetane present in a known sample at periodic intervals. The measurement can take any form known which measures a property relatable to the quantity of dioxetane. Techniques such as spectrophotometry, NMR spectrometry and the like are exemplary. A convenient means is to measure the amount of light produced by reacting a known quantity of dioxetane with a triggering agent under a standard set of conditions. A decrease in the amount or intensity of light emitted signals a loss of dioxetane compound.

Storage stability refers to stability of the dioxetane in both the pure form and as a solution or formulation in a buffer solution. The formulation can also contain various additives for increasing the amount of light produced or for improving the activity of an enzymatic triggering agent. It is desirable that the dioxetane in a formulation not undergo significant decomposition at ambient temperature for a reasonable period of time. Compositions to be used with automated analyzers should desirably be stable for at least 1 week. Upon refrigeration at 0°–5° C., it is desirable that no significant decomposition is observed for at least 2–3 months. More desirably, compositions to be used with automated analyzers should show not more than 2–3% change in the observed indicator of storage stability in about 2–4 weeks.

The solution to the problem of storage stability was found in dioxetanes having the formula:

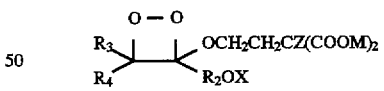

wherein Z is selected from the group consisting of a fluorine atom and an alkyl group of 1–4 carbons and M is selected from hydrogen, an alkali metal ion or a quaternary ammonium or phosphonium ion, wherein $R_3$ and $R_4$ are each selected from acyclic, cyclic and polycyclic organic groups which can optionally be substituted with heteroatoms and which provide stability to the dioxetane, wherein $R_2$ is an aryl ring group selected from phenyl and naphthyl groups which can include additional substituents and wherein X is a protecting group which can be removed by an activating agent to form an oxyanion-substituted dioxetane which decomposes and produces light and two carbonyl-containing compounds, one of which is an oxyanion-substituted ester compound containing two carboxylate groups, as shown below.

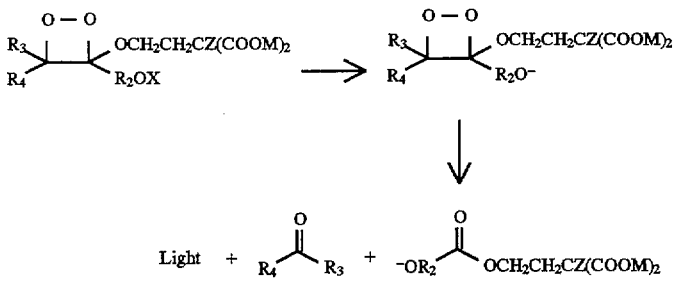

When M is H it is recognized that the respective dioxetane compound will preferably only be used under conditions of pH where the carboxylic acid functions are ionized, i.e. pH≧about 7. Preferably M is an alkali metal ion, most preferably a sodium ion.

The groups $R_3$ and $R_4$ in another embodiment are combined together in a cyclic or polycyclic alkyl group $R_5$ which is spiro-fused to the dioxetane ring, containing 6 to 30 carbon atoms which provides thermal stability and which can include additional non-hydrogen substituents.

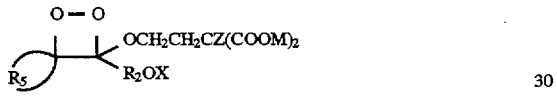

The group $R_5$ is more preferably a polycyclic group, preferably an adamantyl group or a substituted adamantyl group having one or more substituent groups $R_6$ selected from halogens, alkyl, substituted alkyl, alkoxy, substituted alkoxy, carbonyl, carboxyl, phenyl, substituted phenyl, amino and alkylamino groups covalently bonded thereto.

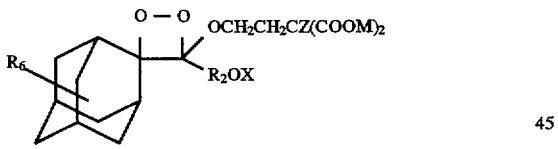

In another preferred embodiment the group $R_2$ is a phenyl or naphthyl group. It is especially preferred that $R_2$ is a phenyl group in which the OX group is oriented meta to the dioxetane ring group as shown below. The phenyl ring may contain additional ring substituents $R_7$ independently selected from halogens, alkyl, substituted alkyl, alkoxy, substituted alkoxy, carbonyl, carboxyl, amino and alkylamino groups. Some exemplary structures include by way of illustration:

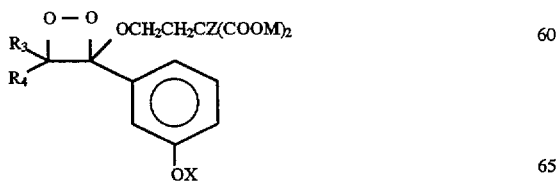

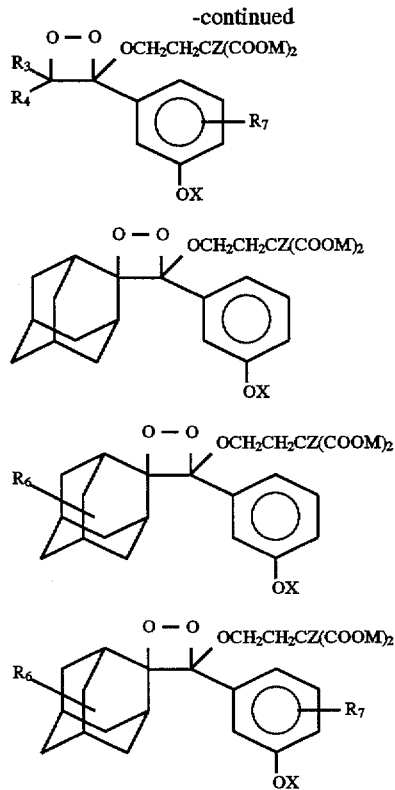

The nature of the OX group is dictated by the triggering agent used in the assay for which it is to be used and may be selected from hydroxyl, $O^-M^+$ wherein M is selected from hydrogen, an alkali metal ion or a quaternary ammonium or phosphonium ion, $OOCR_8$ wherein $R_8$ is selected from the group consisting of an alkyl and aryl groups containing 2 to 8 carbon atoms and optionally containing heteroatoms, $OPO_3^{-2}$ salt, $OSO_3^-$ salt, β-D-galactosidoxy and β-D-glucuronidyloxy groups. The OX group is preferably a $OPO_3^{-2}$ salt group.

Dioxetanes of the present invention having the formula:

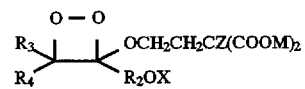

wherein R2, R3, R4, M and Z are as described above can be prepared using methods described in Applicants' co-pending application Ser. No. 08/509,305 and other methods known in the art of dioxetane chemistry. For example, a ketone and ester having the formulas below wherein Y is a replaceable atom or group such as a halogen atom and X' is a replaceable atom or group such as a hydrogen or an alkyl group or a trialkylsilyl group can be coupled by a low-valent titanium reagent to form an intermediate vinyl ether.

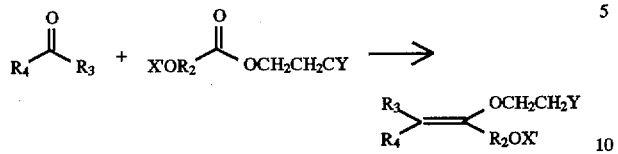

The intermediate vinyl ether is converted in a process of one or more steps to a precursor vinyl ether. The group Y is replaced by a $CZ(COOM)_2$ fragment by reaction with a Z-substituted malonate ester and later saponification of the ester groups. The group X' is converted to the group X in the case where X and X' are not identical by removing X' and reacting with a reagent which adds the X group or a protected form of the X group. For example when X' is H and X is $PO_3Na_2$, treatment with base to deprotonate followed by reaction with a phosphorylating agent produces a phosphate triester-protected vinyl ether which is converted to the phosphate salt by hydrolysis of the triester to the disodium salt. In this multi-step process, two or more operations my occur in the same process step, for example hydrolysis of carboxylic esters and phosphate esters can be effected in the same step.

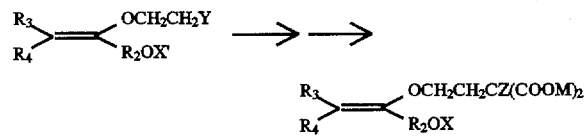

The precursor vinyl ether is directly converted to the dioxetane by known reactions including, for example, addition of singlet oxygen generated by dye sensitization.

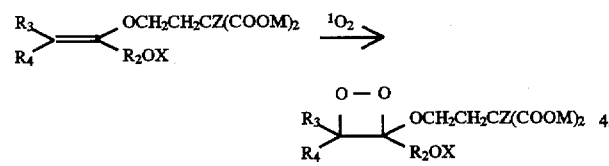

Each of these processes is exemplified by way of illustration in the specific examples below.

Specific Embodiments

A fluoro-substituted analog of dioxetane 1, identified as 3, a chloro-substituted analog 4 and a methyl-substituted analog 5 have been prepared and their storage stability evaluated over several weeks. Storage stability of a solution of 1 was measured for comparison. All solutions were prepared with the same composition, differing only in the identity of the dioxetane. Stability was evaluated by chemiluminescent enzyme assay with a fixed volume of test solution and fixed limiting amount of alkaline phosphatase and measuring the plateau light intensity at 25° C. Unexpectedly, aqueous solutions containing dioxetanes 3 and 5 were substantially more stable than 1, while dioxetane 4 was not. Solutions of dioxetanes 3 or 5 underwent essentially no decomposition after four weeks at 25° C. Surprisingly, the storage stability of dioxetane 4 was actually worse than that of 1.

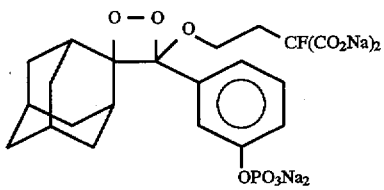

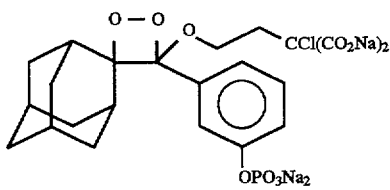

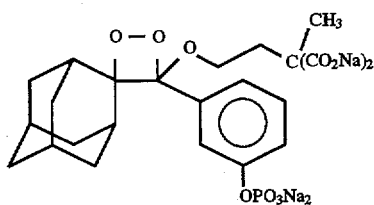

The reasons for this difference in the properties of these four dioxetanes are not presently understood. It is particularly significant that dioxetanes 3 and 4 should show such marked difference in storage stability when they differ structurally only by having different halogen substituents. Applicants are aware of no teachings in the art of dioxetane chemistry to explain or predict these results.

Furthermore, tests on dioxetane 3, showed that, like dioxetane 1, it caused no carryover in the capsule chemistry assay system. Dioxetanes such as 3 and 5 bearing a substituent containing two carboxylate groups and either a fluorine atom or a lower alkyl group and compositions containing such dioxetanes are therefore superior to other known dioxetanes and compositions for use in capsule chemistry analysis systems.

In another aspect of the invention, compositions providing enhanced chemiluminescence are provided. Enhanced compositions are advantageous in assays requiring the highest analytical sensitivity. Increasing the chemiluminescence efficiency of the dioxetane decomposition reaction while maintaining or reducing extraneous light emission from spontaneous dioxetane decomposition is one manner in which sensitivity can be enhanced or improved.

The present invention, therefore, also relates to compositions comprising a cationic enhancer and a stable 1,2-dioxetane as described above having increased storage stability which can be triggered to generate chemiluminescence. Such compositions for providing enhanced chemiluminescence comprise a dioxetane as described above in an aqueous solution, and a non-polymeric cationic enhancer substance which increases the quantity of light produced by reacting the dioxetane with the activating agent compared to the amount which is produced in the absence of the enhancer. It is preferred that the enhancer substance is a dicationic surfactant of the formula:

wherein each of A is independently selected from P and N atoms and wherein Link is an organic linking group containing at least two carbon atoms selected from the group consisting of substituted and unsubstituted aryl, alkyl, alkenyl and alkynyl groups and wherein Link may contain heteroatoms and wherein R is selected from lower alkyl or aralkyl containing 1 to 20 carbon atoms and wherein Y is an anion. It is especially preferred that the enhancer substance is a dicationic surfactant having the formula:

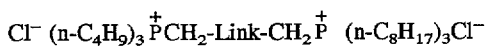

and wherein link is phenylene.

Compositions of the present invention for providing enhanced chemiluminescence may optionally contain at least one fluorescer as a supplementary enhancer. Fluorescers useful are those compounds which are capable of increasing the quantity of light produced through energy transfer. Anionic fluorescers are particularly effective it is believed due to favorable electrostatic interactions with the cationic enhancer. Particularly preferred fluorescers are anionic compounds and include, without limitation, pyranine and fluorescein.

In order to more fully describe the various aspects of the present invention, the following non-limiting examples describing particular embodiments are presented for purposes of illustration of the invention.

EXAMPLES

Example 1

Preparation of Dioxetane 1

This dioxetane was prepared by the sequence of reactions described below. The synthesis up to the intermediate alkene [(3-hydroxyphenyl)-(2-iodoethoxy)methylene]tricyclo[3.3.1.1$^{3,7}$]decane was conducted essentially as described in U.S. Pat. Nos. 5,013,827 and 5,068,339.

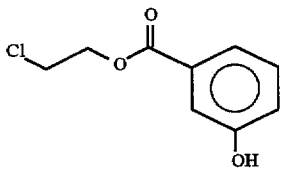

(a) Synthesis of 2-chloroethyl 3-hydroxybenzoate. A solution of 65 g of 3-hydroxybenzoic acid (0.47 mol) in 500 mL of 2-chloroethanol and 3 mL of H$_2$SO$_4$ was refluxed for 4 hours. The cooled solution was diluted with 500 mL of water and extracted with ethyl acetate (3×250 mL). The ethyl acetate was extracted twice with aqueous NaHCO$_3$ and then with water. The ethyl acetate solution was dried and evaporated under reduced pressure yielding 85 g of product as a thick oil; $^1$H NMR (CDCl$_3$) δ3.814 (t,2H, J=6 Hz), 4.569 (t,2H, J=6 Hz), 5.36 (br s,1H), 7.06–7.67 (m,4H).

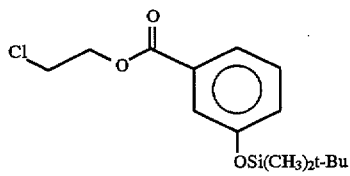

(b) Synthesis of 2-chloroethyl 3-t-butyldimethylsilyloxybenzoate. A solution of 10 g (50 mmol) the ester from step (a), t-butyldimethylsilyl chloride (8.25 g, 55 mmol) and imidazole (4.76 g, 70 mmol) in 100 mL of DMF was stirred under argon for 1 h. The solution was poured into 100 mL of water and extracted with ether (3×50 mL). The combined ether solutions were extracted with 20 mL of water. The organic layer was dried and evaporated giving 18 g of an oil which was purified by column chromatography using 0–2% ethyl acetate in hexane yielding 14.4 g of the product as a colorless oil (91%); $^1$H NMR (CDCl$_3$) δ0.218 (s,6H), 0.995 (s,9H), 3.81 (t,2H), 4.56 (t,2H), 7.05–7.65 (m,4H).

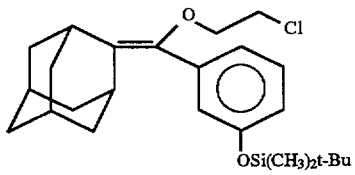

(c) Synthesis of [(2-chloroethoxy)-(3-t-butyldimethylsilyloxyphenyl)methylene]tricyclo[3.3.1.1$^{3,7}$] decane. A three neck flask was purged with argon and charged with 400 mL of anhydrous THF. Titanium trichloride (48 g, 0.3 mol) was added with stirring and the flask was cooled in an ice bath. Lithium aluminum hydride (6.0 g, 0.16 mol) was added in small portions causing a brief exothermic reaction. After all of the LAH was added, the cooling bath was removed and the mixture warmed to room temperature. Triethylamine (30 mL) was added and the black mixture was refluxed for 1.5 hours under argon. A solution of adamantanone (14 g, 93 mmol) and 2-chloroethyl 3-t-butyldimethylsilyloxybenzoate (10 g, 31 mmol) in 50 mL of dry THF was added dropwise while reflux was continued. After an additional 10 min, TLC (5% ethyl acetate in hexane) indicated conversion of the ester to new material so the mixture was cooled and diluted with 3 L of hexane. The hexane was decanted, filtered through filter paper and evaporated leaving an oil which was purified by column chromatography on silica gel, eluting with 0–3% ethyl acetate in hexane yielding 8.68 g of alkene (65% based on ester); $^1$H NMR (CDCl$_3$) δ0.195 (s,6H), 0.983 (s,9H), 1.78–1.98 (m,12H), 2.65 (br s,1H), 3.334 (br s,1H), 3.55 (t,2H), 3.66 (t,2H), 6.85–7.29 (m,4H).

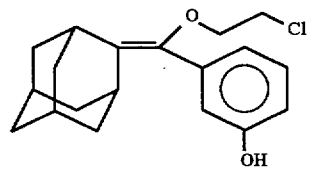

(d) Synthesis of [(2-chloroethoxy)-(3-hydroxyphenyl)methylene]tricyclo[3.3.1.1$^{3,7}$]decane. The silyl-protected alkene (8.0 g, 19 mmol) was dissolved in 100 mL of dry THF and reacted with 5.2 g of tetrabutylammonium fluoride. After stirring 15 min, the solution was evaporated and the residue partitioned between 100 mL of ether and 100 mL of water. The water solution was extracted with three 100 mL portions of ether. The combined organic solutions were washed with three 100 mL portions of water, dried and evaporated. The residue (6.5 g) was chromatographed using 5–20% ethyl acetate in hexane. This produced 4.78 g of oily product; $^1$H NMR (CDCl$_3$) δ1.78–1.98 (m,12H), 2.67 (br s,1H), 3.34 (br s,1H), 3.55 (t,2H), 3.69 (t,2H), 4.91 (br s,1H), 6.77–7.19 (m, 4H).

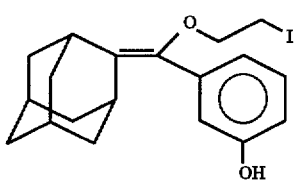

(e) Synthesis of [(3-hydroxyphenyl)-(2-iodoethoxy) methylene]tricyclo[3.3.1.1$^{3,7}$]decane. The chloroethoxy alkene (2 g) was dissolved in 30 mL of anhydrous acetone. Sodium iodide (9.3 g) was added and the solution refluxed for 4 days. After cooling, the precipitate was filtered and washed with a little $CH_2Cl_2$. The washings and acetone were combined and evaporated. The residue was redissolved in $CH_2Cl_2$ and washed with water and dried. The crude material was chromatographed using 25% ethyl acetate in hexane. The yield was 93% of a slightly yellow oil; $^1$H NMR (CDCl$_3$) δ1.78–1.98 (m,12H), 2.65 (br s,1H), 3.19 (t,2H), 3.35 (br s,1H), 3.69 (t,2H), 4.90 (br s,1H), 6.75–7.24 (m,4H).

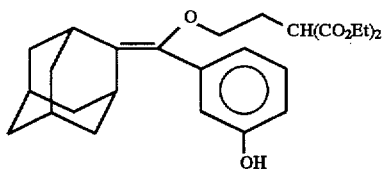

(e) Synthesis of [((3,3-biscarboethoxy)propoxy)-(3-hydroxyphenyl)methylene]tricyclo[3.3.1.1$^{3,7}$]decane. Diethyl malonate (3.12 g) was dissolved in 25 mL of absolute ethanol containing 11.65 mL of a 21% solution of sodium ethoxide in ethanol. The solution was cooled in an ice bath and the iodoethoxy alkene (3.2 g) was added dropwise as an ethanol solution to the reaction mixture. The reaction was refluxed over night. After cooling, the mixture was evaporated and redissolved in ethyl acetate. The ethyl acetate solution was extracted with water, dried and evaporated. The crude material was chromatographed using 15–25% ethyl acetate in hexane. The yield of product was typically 42–48%; $^1$H NMR (CDCl$_3$) δ1.24 (t,6H), 1.78–1.97 (m, 12H), 2.11–2.17 (q,2H), 2.66 (br s,1H), 3.21 (br s,1H), 3.42 (t,2H), 3.63 (t,1H), 4.13–4.22 (m,4H), 5.00 (br s,1H), 6.75–7.21 (m,4H).

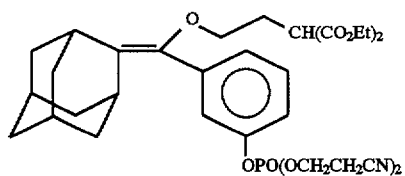

(f) Synthesis of [((3,3-biscarboethoxy)propoxy)-(3-(bis-(2-cyanoethyl)phosphoryloxy)phenyl)methylene]tricyclo [3.3.1.1$^{3,7}$]decane. A flask containing 30 mL of $CH_2Cl_2$ under a layer of argon was cooled in an ice bath. Pyridine (6.95 mL) was added followed by slow addition of POCl$_3$ (2.47 mL) and stirring continued for 15 min. A solution of the alkene from step (e) in 10 mL of $CH_2Cl_2$ and 5 mL of pyridine was added dropwise. The ice bath was removed and the solution stirred for 2 hours. To this solution was added 6.95 mL of pyridine and 6.1 g of 2-cyanoethanol. The reaction mixture was stirred over night resulting in formation of a yellow precipitate. The mixture was added to 200 mL of $CH_2Cl_2$ and washed with 3×75 mL of water. The $CH_2Cl_2$ extract was dried and evaporated. The crude product was purified by chromatography using 70% ethyl acetate in hexane. $^1$H NMR (CDCl$_3$) δ1.25 (t,6H), 1.74–1.98 (m, 12H), 2.10–2.17 (q,2H), 2.61 (br s,1H), 2.81 (t,4H), 3.21 (br s,1H), 3.42 (t,2H), 3.59 (t,1H), 4.11–4.22 (m,4H), 4.39–4.46 (m,4H), 7.14–7.36 (m,4H).

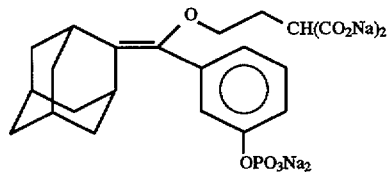

(g) Synthesis of [(3,3-biscarboxypropoxy)-(3-phosphoryloxyphenyl)methylene]tricyclo[3.3.1.1$^{3,7}$] decane, tetrasodium salt. The alkene (3.9 g) from step (f) was dissolved in 12 mL of acetone. A solution of 1.04 g of sodium hydroxide in 3 mL of water was added. The solution was stirred for 19 hours during which time 3 mL of acetone was added to the flask. The liquid was decanted and the solid was washed with more acetone. After drying under vacuum, a white solid was obtained. $^1$H NMR (D$_2$O) δ1.72–2.07 (m, 14H), 2.59 (br s,1H), 3.14–3.18 (m,2H), 3.40 (t,2H), 7.01–7.34 (m,4H).

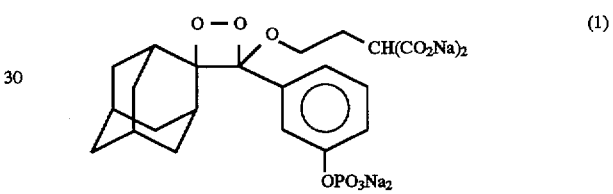

(1)

(h) Synthesis of [4-(3,3-biscarboxy)propoxy)-4-(3-phosphoryloxyphenyl)]spiro[1,2-dioxetane-3,2'-tricyclo [3.3.1.1$^{3,7}$]decane], tetrasodium salt (1). The alkene (2.5 g) from step (g) was dissolved in 50 mL of D$_2$O. Polymer-bound Rose Bengal (500 mg) was suspended in 50 mL of p-dioxane and added to the water solution. The reaction mixture was cooled to 5°–7° C., oxygen bubbling was started and the mixture irradiated with a sodium lamp through a 5 mil sheet of KAPTON (DuPont). After a total of 18 hours, the polymer beads were filtered off, the vessel was washed with methanol and the combined solution concentrated to 25 mL. The remaining solvent was removed by lyophilization.

Example 2

Preparation of Dioxetane 2

This dioxetane was prepared by the sequence of reactions described below. The synthesis up to the intermediate alkene [(3-carboxypropoxy)-(3-hydroxyphenyl)methylene] tricyclo-[3.3.1.1$^{3,7}$]decane was conducted essentially as described in published European Patent Application No. 91113601.8.

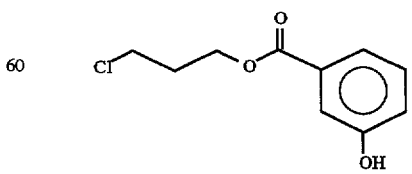

(a) Synthesis of 3-chloropropyl 3-hydroxybenzoate. 3-Chloro-1-propanol (161.6 g, 1.71 mol) was refluxed with 3-hydroxy-benzoic acid (40.0 g, 0.29 mol) and a catalytic amount of sulfuric acid for a total of 9 hours. The excess alcohol was removed by vacuum distillation. The resulting orange oil was diluted with 400 mL of water and neutralized to pH 7. The solution was extracted with ethyl acetate (3×250 mL). The organic layer was washed with 100 mL of brine and dried over anhydrous sodium sulfate, filtered and concentrated under reduced pressure. The product was purified by column chromatography with to give 67.5 g of product which contained a small amount of the starting alcohol: $^1$H NMR (CDCl$_3$) δ2.24 (quint, 2H), 3.70 (t, 2H), 4.48 (t, 2H, J=6 Hz), 5.55 (s, 1H), 7.05–7.63 (m, 4H).

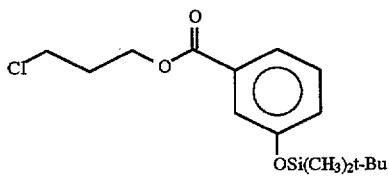

(b) Synthesis of 3-chloropropyl 3-(tert-butyldimethylsiloxy) benzoate. 3-Chloropropyl 3-hydroxybenzoate (67.5 g) was dissolved in anhydrous DMF (100 mL) followed by and t-butyldimethylsilyl chloride (52.11 g). The reaction mixture was stirred under Ar until the starting material was consumed. The reaction mixture was diluted with water (500 mL) and extracted with hexane (4×750 mL) and then with 2×250 mL of ethyl acetate. The combined organic solutions were dried over sodium sulfate, concentrated under reduced pressure and partitioned a second time between 500 mL of water and hexane. Drying the organic solution and evaporating gave the silylated ester as white crystals (89.64 g, 94%). $^1$H NMR (CDCl$_3$) δ0.219 (s, 6H), 0.998 (s, 9H), 2.24 (quint, 2H), 3.70 (t, 2H), 4.470 (t, 2H), 7.03–7.64 (m, 4H).

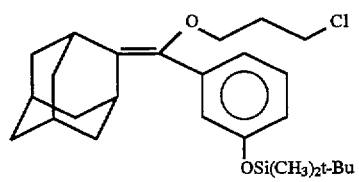

(c) Synthesis of [(3-tert-butyldimethylsilyloxylphenyl)-(3-chloropropoxy)methylene]tricyclo[3.3.1.1$^{3,7}$]decane. Titanium trichloride (25.8 g, 0.167 mol) was added to dry THF (500 mL) in a dried 3 L three-necked flask under a head of Ar at 0° C. Lithium aluminum hydride (3.01 g, 0.084 mol) was added in small portions with vigorous stirring. The reaction mixture was warmed to room temperature and 23.3 mL of triethylamine was added dropwise. After the addition was completed, the reaction mixture was refluxed for 2 h. Heating was stopped and a solution of 3-chloropropyl 3-(t-butyldimethylsilyloxy)benzoate (5.28 g, 0.016 mol) and adamantanone (7.23 g, 0.048 mol) in 100 mL of dry THF was added dropwise to the refluxing mixture over a 45 min period. The reaction mixture was stirred over night at room temperature. The black mixture was diluted with water and extracted with 3×300 mL of hexane. The combined organic solutions were filtered, dried over sodium sulfate and concentrated under reduced pressure. The residue was partially purified by flash chromatography (2% ethyl acetate/hexane) to give the product as a viscous oil which was taken on to the next step. 1H NMR (CDCl$_3$) δ0.200 (s, 6H), 0.988 (s, 9H), 1.66–2.01 (m, 14H), 2.63 (br s, 1H), 3.23 (br s, 1H), 3.538 (t, 2H, J=5.7 Hz), 3.640 (t, 2H, J=6.6 Hz), 6.75–7.22 (m, 4H).

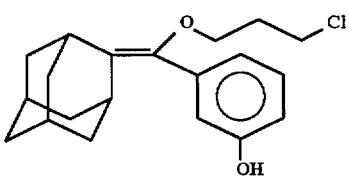

(d) Synthesis of [(3-Chloropropoxy)-(3-hydroxyphenyl)methylene]tricyclo[3.3.1.1$^{3,7}$]decane. The silyl-protected alkene (5.36 g slightly impure) was dissolved in 75 mL of dry THF and placed under Ar. TBAF (4.16 g, 13.2 mmol) was added and the reaction mixture stirred for 30 min at room temperature. The solvent was evaporated and the residue was dissolved in 100 mL of water. The solution was extracted with 3×125 mL of ether and the organic layer was washed with brine and dried over Na$_2$SO$_4$. Removal of solvent under reduced pressure and column chromatography with 10% ethyl acetate in hexane afforded 2.05 g of the deprotected alkene. $^1$H NMR (CDCl$_3$) δ1.78–2.01 (m, 14H), 2.65 (br s, 1H), 3.22 (br s, 1H), 3.541 (t, 2H, J=6 Hz), 3.644 (t, 2H, J=6 Hz), 5.30 (s, 1H), 6.75–7.24 (m, 4H).

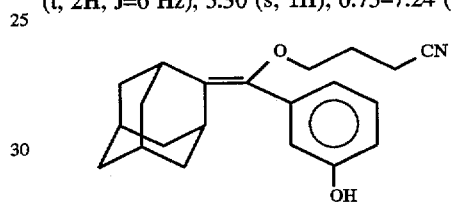

(e) Synthesis of [(3-cyanopropoxy)-(3-hydroxyphenyl)methylene]tricyclo [3.3.1.1$^{3,7}$]decane. Sodium cyanide (300 mg, 6.1 mmol) was added to a solution of the chloroalkene (815 mg, 2.4 mmol) in anhydrous DMSO (4 mL) forming a purple solution which was heated to 120° C. for 1 hr. The cooled solution was diluted with ether (50 mL) and washed with water (3×25 mL). The ether layer was dried and concentrated under reduced pressure. The product was obtained as an oil in 85% yield. $^1$H NMR (CDCl$_3$) δ1.77–1.97 (m, 14H), 2.49 (t, 2H), 2.65 (br s, 1H), 3.19 (br s, 1H), 3.49 (t, 2H), 5.04 (s, 1H), 6.75–7.24 (m, 4H).

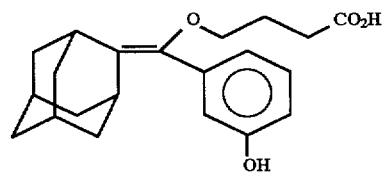

(f) Synthesis of [(3-carboxypropoxy)-(3-hydroxyphenyl)methylene]tricyclo[3.3.1.1$^{3,7}$]decane. Sodium hydroxide (7 mL of 2N solution) was added to the nitrile (0.67 g, 2 mmol) and the reaction mixture was refluxed for 36 h. The solution was cooled to room temperature and neutralized with acetic acid (1 eq.). The mixture was extracted with ethyl acetate. The organic layer was washed three times with water, then brine and dried over sodium sulfate. The product was concentrated under reduced pressure to an oil affording the acid (0.64 g, 91%). $^1$H NMR (CDCl$_3$) δ1.78–1.97 (m, 14H), 2.47 (t, 2H), 2.65 (br s, 1H), 3.22 (br s, 1H), 3.45 (t, 2H), 5.83 (s, 1H), 6.74–7.22 (m, 4H).

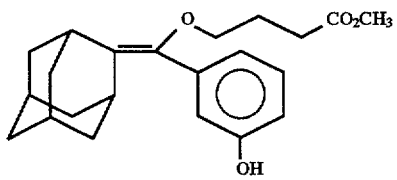

(g) Synthesis of [(3-carbomethoxypropoxy)-(3-hydroxyphenyl)methylene]tricyclo [3.3.1.1$^{3,7}$]decane. The carboxylic acid (660 mg, 1.9 mmol) from the previous step was dissolved in 10 mL of $CH_2Cl_2$. DCC (597 mg, 2.8 mmol), DMAP (23 mg) and methanol (1 mL) were added and the solution stirred for 18 hours. The mixture was filtered to remove solid material and evaporated. The solid residue was suspended in ether and filtered. The product was purified by column chromatography with 30% ethyl acetate in hexane. $^1$H NMR ($CDCl_3$) δ1.77–1.96 (m, 14H), 2.42 (t, 2H), 2.65 (br s, 1H), 3.22 (br s, 1H), 3.41 (t, 2H), 3.65 (s,3H), 5.15 (br s,1H), 6.74–7.22 (m, 4H).

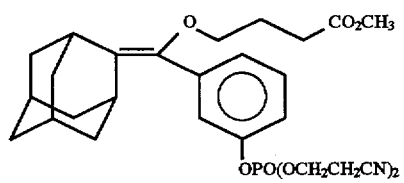

(h) Synthesis of [(3-carbomethoxypropoxy)-(3-(bis-(2-cyanoethyl)phosphoryloxy)phenyl)methylene]tricyclo [3.3.1.1$^{3,7}$]decane. A flask containing 5 mL of $CH_2Cl_2$ under a layer of argon was cooled in an ice bath. Pyridine (0.5 mL) was added followed by slow addition of $POCl_3$ (465 mg) and stirring continued for 15 min. A solution of the alkene (360 mg) from step (g) in 0.5 mL of 1:1 $CH_2Cl_2$/pyridine was added dropwise. The ice bath was removed and the solution stirred for 135 min. To this solution was added 1.0 mL of pyridine and 0.69 mL of 2-cyanoethanol. The reaction mixture was stirred for 4 hours resulting in formation of a white precipitate. TLC showed formation of two materials. Adding an additional 200 μL of cyanoethanol caused the precipitate to dissolve but stirring over night was without effect. The solution was evaporated to dryness and the crude product purified chromatographically. $^1$H NMR ($CDCl_3$) δ1.79–1.98 (m, 14H), 2.41 (t,2H), 2.61 (br s,1H), 2.80 (m,4H), 3.23 (br s,1H), 3.41 (t,2H), 3.65 (s,3H), 4.32–4.48 (m,4H), 7.15–7.37 (m,4H).

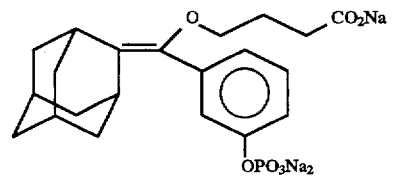

(i) Synthesis of [(3-carboxypropoxy)-(3-phosphoryloxyphenyl)methylene]tricyclo[3.3.1.1$^{3,7}$] decane, trisodium salt. The alkene (142 mg) from step (h) was dissolved in 4 mL of acetone. A solution of 36.4 mg of sodium hydroxide in <1 mL of water was added. The solution was stirred for 20 hours. causing formation of a precipitate. The liquid was decanted and the solid washed with more acetone followed by methanol. After drying under vacuum, 100 mg of a white solid was obtained. $^1$H NMR ($D_2O$) δ1.71–1.95 (m,14H), 2.23 (t,2H), 2.62 (br s,1H), 3.18 (br s,1H), 3.53 (t,2H), 7.04–7.36 (m,4H).

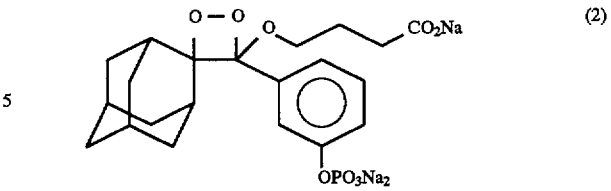

(j) Synthesis of [4-(3-carboxypropoxy)-4-(3-phosphoryloxyphenyl)]spiro [1,2-dioxetane-3,2'-tricyclo [3.3.1.1$^{3,7}$]decane] (2). The alkene (26.8 mg) from step (i) was dissolved in 1.5 mL of $D_2O$. Polymer-bound Rose Bengal (75 mg) was suspended in 1.5 mL of p-dioxane-$d_8$ and added to the water solution. The reaction mixture was cooled to 5°–7° C., oxygen bubbling was started and the mixture irradiated with a sodium lamp through a 5 mil KAPTON filter. After a total of 30 min, $^1$H NMR indicated the reaction to be complete (disappearance of peak at δ2.6) so the polymer beads were filtered off.

Example 3

Preparation of Dioxetane 3

This dioxetane was prepared by the sequence of reactions described below. The synthesis up to the intermediate alkene [(3-hydroxyphenyl)-(2-iodoethoxy)methylene]tricyclo [3.3.1.1$^{3,7}$]decane was conducted as described in Example 1.

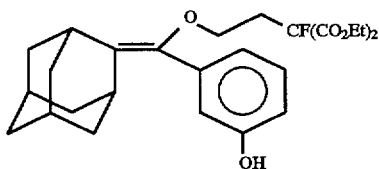

(a) Synthesis of [((3,3-biscarboethoxy)-3-fluoropropoxy)-(3-hydroxyphenyl)methylenetricyclo[3.3.1.1$^{3,7}$]decane. Sodium hydride (75 mg of a 60% dispersion in oil) was washed free of oil with hexane, dried under vacuum and added to 4 mL of anhydrous DMSO. Diethyl fluoromalonate (0.3 g) was added and the suspension stirred under Ar for 15 min. A solution of the iodoethoxy alkene (0.5 g) in 5 mL of anhydrous DMSO was added to the reaction mixture. The reaction was heated to 100° C. and stirred for 2 h. After cooling, the mixture was diluted with 30 mL of ethyl acetate. The ethyl acetate solution was extracted 3–4 times with water, dried and evaporated. The crude material was chromatographed using 5–20% ethyl acetate in hexane. The desired compound (0.25 g) was obtained in 45% yield: $^1$H NMR ($CDCl_3$) δ1.28 (t,6H), 1.66–1.95 (m,12H), 2.45 (t,1H), 2.52 (t,1H), 2.67(br s,1H), 3.20 (br s,1H), 3.52(t, 2H), 4.23–4.30 (q,4H), 6.74–7.22 (m,4H).

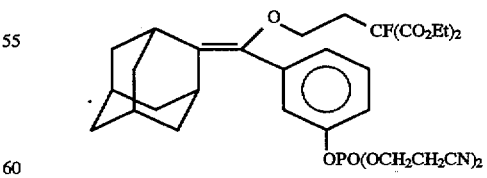

(b) Synthesis of [((3,3-biscarboethoxy)-3-fluoropropoxy-(3-(bis-(2-cyanoethyl)phosphoryloxy)phenyl)methylene] tricyclo[3.3.1.1$^{3,7}$]decane. A flask containing 10 mL of $CH_2Cl_2$ under a layer of argon was cooled in an ice bath. Pyridine (1.71 mL) was added followed by slow addition of $POCL_3$ (0.61 mL) and stirring continued for 15 min. A solution of the alkene (0.972 g) from step (a) in 10 mL of CH$_2$Cl$_2$ was added dropwise. The ice bath was removed and the solution stirred for 2.5 h. To this solution was added 1.71 mL of pyridine and 1.44 mL of 2-cyanoethanol. The reaction mixture was stirred for 3 h resulting in formation of a white precipitate. The mixture was diluted with CH$_2$Cl$_2$ and washed with 4×50 mL of water. The CH$_2$Cl$_2$ extract was dried and evaporated. The crude product was purified by chromatography using 75% ethyl acetate in hexane. A total of 1.2 g of an oil (88%) was obtained: $^1$H NMR (CDCl$_3$) δ1.29 (s,6H), 1.79–1.97 (m,12H), 2.46–2.53 (2t,2H), 2.63 (br s,1H), 2.83 (t,4H), 3.20 (br s,1H), 3.50 (t,2H), 4.24–4.31 (q,4H), 4.35–4.51 (m,4H), 7.13–7.36 (m,4H); $^{31}$P NMR (CDCl$_3$) δ−9.49 (p).

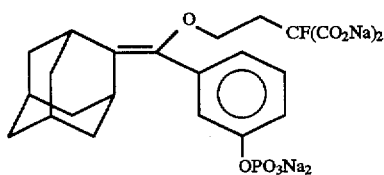

(c) Synthesis of [(3,3-biscarboxy-3-fluoropropoxy)-(3-phosphoryloxyphenyl)methylene]tricyclo[3.3.1.1$^{3,7}$] decane, tetrasodium salt. The alkene (1.2 g) from step (b) was dissolved in 20 mL of acetone. A solution of 297 mg of sodium hydroxide in 4 mL of water was added. The solution was stirred over night during which time a precipitate formed. The liquid was decanted and the solid washed with 10×5 mL of acetone. After drying under vacuum, a white solid (1.0 g) was obtained: $^1$H NMR (D$_2$O) δ1.75–1.89 (m,12H), 2.29 (t,2H), 2.37 (t,2H), 2.57 (br s,1H), 3.12 (br s,1H), 3.56 (t,2H), 6.99–7.30 (m,4H); $^{31}$P NMR (D$_2$O) δ0.69 (s).

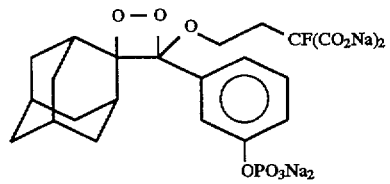

(3)

(d) Synthesis of [4-(3,3-biscarboxy)-3-fluoropropoxy)-4-(3-phosphoryloxyphenyl)]spiro[1,2-dioxetane-3,2'-tricyclo [3.3.1.1$^{3,7}$]decane], tetrasodium salt (3). The alkene (348.6 mg) from step (c) was dissolved in 10 mL of D$_2$O. Polymer-bound Rose Bengal (500 mg) was suspended in 10 mL of p-dioxane and added to the water solution. The reaction mixture was cooled to 5°–8° C., oxygen bubbling was started and the mixture irradiated with a sodium lamp through a 5 mil KAPTON filter. After a total of 2.5 h, the polymer beads were filtered off and the solution was evaporated to dryness producing a white solid (3). $^1$H NMR (D$_2$O) δ0.93–1.79 (m, 12H), 2.19 (br s,1H), 2.41–2.49 (m,2H), 2.97 (br s,1H), 3.40–3.49 (m,2H), 7.19–7.42 (m,4H); $^{31}$P NMR (D$_2$O) δ0.575 (s).

Example 4

Preparation of Dioxetane 4

This dioxetane was prepared by the sequence of reactions described below. The synthesis up to the intermediate alkene [(3-hydroxyphenyl)-(3,3-biscarboethoxy) propoxymethylene]tricyclo[3.3.1.1$^{3,7}$]decane was conducted as described in Example 1.

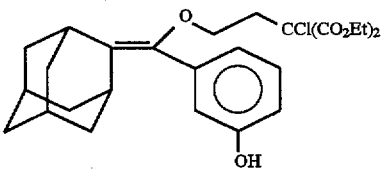

(a) Synthesis of [((3,3-biscarboethoxy)-3-chloropropoxy)-(3-hydroxyphenyl)methylenetricyclo[3.3.1.1$^{3,7}$]decane. A solution of (3,3-biscarboethoxypropoxy)-(3-hydroxyphenyl)methylenetricyclo[3.3.1.1$^{3,7}$]decane (1.2 g) in 10 mL of dry THF was added to a 2.4 eq. of LDA in 25–30 mL of dry THF at −78° C. under argon. The reaction was stirred for 30 min at −78° C. and treated with a solution of N-chlorosuccinimide (0.58 g) in 15 mL of dry THF. The reaction was allowed to warm to room temperature over an hour and stirred for an additional hour. The THF was removed in vacuo and the residue dissolved in 100 mL of ethyl acetate. The organic solution was washed with water, dried and evaporated. The crude material was separated by column chromatography. $^1$H NMR (CDCl$_3$) δ1.23 (t,6H), 1.7–2.00 (m,12H), 2.57 (t,2H), 2.65 (br s,1H), 3.2 (br s,1H), 3.56 (t,2H), 4.22 (q,4H), 6.65–7.25 (m,4H).

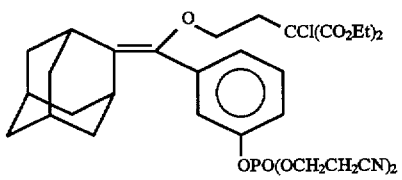

(b) Synthesis of [((3,3-biscarboethoxy)-3-chloropropoxy(3-(bis-(2-cyanoethyl)phosphoryloxy)phenyl)methylene] tricyclo[3.3.1.1$^{3,7}$]decane. A flask containing 25 mL of CH$_2$Cl$_2$ under a layer of argon was cooled in an ice bath. Pyridine (1.5 g) was added followed by slow addition of POCl$_3$ (1.82 g) and stirring continued for 15 min. A solution of the alkene (1.5 g) from step (a) and 1.5 g of pyridine in 25 mL of CH$_2$Cl$_2$ was added dropwise. The ice bath was then removed and the solution stirred for 1 h. The solution was again cooled with an ice bath and treated sequentially with 3.0 g of pyridine and 2.8 g of 2-cyanoethanol. The reaction mixture was stirred for 12–15 h resulting in formation of a white precipitate. The mixture was diluted with CH$_2$Cl$_2$ and washed with water. The CH$_2$Cl$_2$ extract was dried and evaporated. The crude product was purified by chromatography using 50% ethyl acetate in hexane. A total of 1.4 g of product was obtained an oil: $^1$H NMR (CDCl$_3$) δ1.278 (t,6H), 1.80–1.97 (m,12H), 2.565 (t,2H), 2.63 (br s,1H), 2.826 (t,4H), 3.20 (br s,1H), 3.556 (t,2H), 4.271 (q,4H), 4.40–4.47 (m,4H), 7.15–7.36 (m,4H).

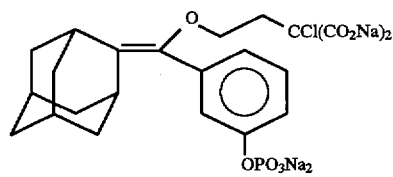

(c) Synthesis of [(3,3-biscarboxy-3-chloropropoxy)-(3-phosphoryloxyphenyl)methylene]tricyclo[3.3.1.1$^{3,7}$] decane, tetrasodium salt. The alkene (0.9 g) from step (b) was dissolved in 25 mL of acetone. A solution of 0.22 g of sodium hydroxide in 3 mL of water was added. The solution was stirred over night during which time a precipitate formed. The liquid was decanted and the solid triturated with acetone. The white solid was filtered, washed further with acetone and dried under vacuum: $^1$H NMR (D$_2$O) δ1.77–1.92 (m,12H), 2.422 (t,2H), 2.59 (br s,1H), 3.15 (br s,1H), 3.635 (t,2H), 7.02–7.33 (m,4H).

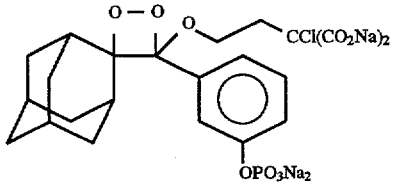

(4)

(d) Synthesis of [4-(3,3-biscarboxy)-3-chloropropoxy)-4-(3-phosphoryloxyphenyl)]spiro[1,2-dioxetane-3,2'-tricyclo [3.3.1.1$^{3,7}$]decane], tetrasodium salt (4). The alkene (35 mg) from step (c) was dissolved in 1.0 mL of D$_2$O. Polymer-bound Rose Bengal (500 mg) was soaked in 1.0 mL of p-dioxane-d$_8$ for 5 min and then added to the water solution. The reaction mixture was cooled to 0° C., oxygen bubbling was started and the mixture irradiated with a sodium lamp through a 5 mil KAPTON filter for 45 min to produce 4 as determined by NMR. The mixture was filtered and the solution diluted in buffer for enzyme assay: $^1$H NMR (D$_2$O) δ1.05–1.96 (m, 12H), 2.19 (br s,1H), 2.60–2.62 (m,2H), 3.07 (br s,1H), 3.56–3.58 (m,2H), 7.25–7.44 (m,4H).

Example 5

Preparation of Dioxetane 5

This dioxetane was prepared by the sequence of reactions described below. The synthesis up to the intermediate alkene [(3-hydroxyphenyl)-(2-iodoethoxy)methylene]tricyclo [3.3.1.1$^{3,7}$]decane was conducted as described in Example 1.

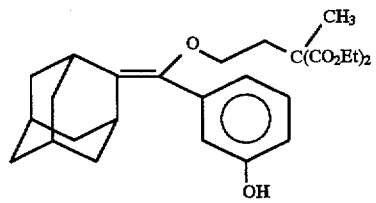

(a) Synthesis of [((3,3-biscarboethoxybutoxy)-(3-hydroxyphenyl)methylenetricyclo[3.3.1.1$^{3,7}$]decane. Sodium hydride (0.866 g of a 60% dispersion in oil) was washed free of oil with hexane, dried under vacuum and added to 15 mL of anhydrous DMSO. Diethyl methylmalonate (2.4 g) was added and the suspension stirred under Ar for 15 min. A solution of the iodoethoxy alkene (2.8 g) in 15 mL of anhydrous DMSO was added to the reaction mixture. The reaction was heated to 100° C. and stirred for 2 h. After cooling, the mixture was diluted with 30 mL of ethyl acetate. The ethyl acetate solution was extracted 3–4 times with water, dried and evaporated. The crude material was chromatographed using 5–20% ethyl acetate in hexane. The desired compound (0.80 g) was obtained in 25% yield: $^1$H NMR (CDCl$_3$) δ1.208 (t,6H), 1.347 (s,3H), 1.76–1.96 (m,12H), 2.20 (t,2H), 2.66 (br s,1H), 3.20 (br s,1H), 3.41 (t,2H), 4.09–4.17 (q,4H), 6.78–7.26 (m,4H)

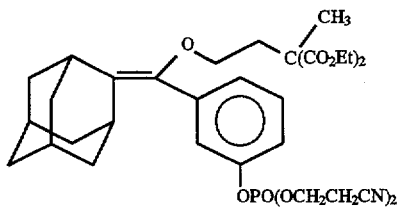

(b) Synthesis of [((3,3-biscarboethoxybutoxy-3-(bis-(2-cyanoethyl)phosphoryloxy)phenyl)methylene]tricyclo [3.3.1.1$^{3,7}$]decane. A flask containing 15 mL of CH$_2$Cl$_2$ under a layer of argon was cooled in an ice bath. Pyridine (1.38 g) was added followed by slow addition of POCl$_3$ (0.8 g) and stirring continued for 15 min. A solution of the alkene (0.8 g) from step (a) in 15 mL of CH$_2$Cl$_2$ was added dropwise. The ice bath was removed and the solution stirred for 1 h. To this solution was added 1.38 g of pyridine and 1.24 g of 2-cyanoethanol. The reaction mixture was stirred for 12–15 h resulting in formation of a white precipitate. The mixture was diluted with CH$_2$Cl$_2$ and washed with 4×50 mL of water. The CH$_2$Cl$_2$ extract was dried and evaporated. The crude product was purified by chromatography using 75% ethyl acetate in hexane. A total of 0.55 g of an oil (50%) was obtained: $^1$H NMR (CDCl$_3$) δ1.208 (t, 6H), 1.34 (s,3H), 1.78–1.97 (m,12H), 2.18 (t,2H), 2.61 (br s,1H), 2.81 (t,4H), 3.21 (br s,1H), 3.41 (t,2H), 4.09–4.16 (q,4H), 4.37–4.46 (m,4H), 7.14–7.34 (m,4H).

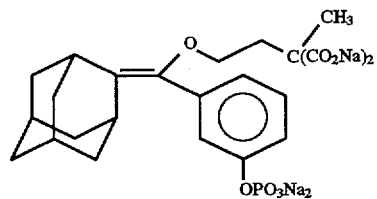

(c) Synthesis of [(3,3-biscarboxybutoxy)-(3-phosphoryloxyphenyl)methylene]tricyclo[3.3.1.1$^{3,7}$] decane, tetrasodium salt. The alkene (0.47 g) from step (b) was dissolved in 14 mL of acetone. A solution of 0.117 g of NaOH in 1.5 mL of water was added. The solution was stirred over night during which time a precipitate formed. The liquid was decanted and the solid washed with 10×5 mL of acetone. After drying under vacuum, a white solid (0.383 g, 92%) was obtained: $^1$H NMR (D$_2$O) δ1.09 (s,3H), 1.75–1.90 (m,12H), 2.00 (t,2H), 2.57 (br s,1H), 3.13 (br s,1H), 3.47 (t,2H), 7.01–7.29 (m,4H).

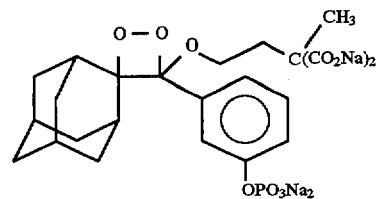

(5)

(d) Synthesis of [4-(3,3-biscarboxybutoxy)-4-(3-phosphoryloxyphenyl)]spiro[1,2-dioxetane-3,2'-tricyclo [3.3.1.1$^{3,7}$]decane], tetrasodium salt (5). The alkene (65 mg) from step (c) was dissolved in 3 mL of D$_2$O. Polymer-bound Rose Bengal (35 mg) was suspended in 3 mL of p-dioxane and added to the water solution. The reaction mixture was cooled to 5°–8° C., oxygen bubbling was started and the mixture irradiated with a sodium lamp through a 5 mil KAPTON filtered for 1 h to produce (5). The polymer beads were filtered off and the solution used for preparing stock solutions for testing. $^1$H NMR (D$_2$O) δ0.92–1.33 (m,5H), 1.38–2.21 (m, 13H), 2.92 (br s,1H), 3.19–3.32 (m,2H), 7.14–7.73 (m,4H).

Example 6

Discovery of Reagent Carryover Problem in Capsule Chemistry Analysis System

The experiments described below were performed on a prototype capsule chemistry analysis system essentially as described by Kumar et al in U.S. Pat. No. 5,399,497, with the detection system configured to measure light emission (luminescence). The method and apparatus comprises feeding a stream of fluid segments through a Teflon tube, where the tube has an isolating layer of fluorocarbon oil on the inner surface. Sample and reagents are aspirated into this tube, and the resulting liquid segments are moved through the tube. Separation steps and washing steps which are required by heterogeneous immunoassay methods were facilitated by means of magnets, which transferred magnetic particles from one aqueous segment to another. The detection system was comprised of a photon counter and a fiber optic read head, in which the fibers were radially arranged around the Teflon tube to maximize the efficiency of light collection.

The TECHNICON IMMUNO 1® TSH method (Bayer Corporation, Tarrytown, N.Y., USA) was used as a representative immunoassay method for the testing of luminogenic reagents. The method principle involved incubation of a specimen containing the antigen TSH with a first reagent (R1), which contained a fluorescein-labeled antibody, and simultaneously with a second reagent (R2), which contained an antibody-alkaline phosphatase (ALP) conjugate. Each antibody was specific for a different epitope on the TSH antigen, so that formation of a "sandwich" was promoted between these two antibodies and the TSH antigen. Magnetic particles containing bound anti-fluorescein were used to capture the sandwich, and the particles were subsequently washed to remove unbound reagents. The particles were then exposed to the luminogenic reagent, which contained a substrate for ALP, and luminescence was measured.

The luminogenic R3 reagent was comprised of 0.2 mM CSPD (disodium 3-(4-methoxyspiro{1,2-dioxetane-3,2'-(5'-chloro)tricyclo[3.3.1.1$^{3,7}$]decan)}-4-yl)phenyl phosphate, (Tropix, Inc., Bedford, Mass., USA), 3 mM pyranine (hydroxypyrenesulfonic acid), 1 mM MgCl$_2$, 1M diethanolamine buffer (pH 10.0), 0.1% Triton X-100 and 0.1% NaN$_3$. The sequence of events on the capsule chemistry analysis system is depicted in FIG. 1 of the drawings. The fluid capsule or test package was comprised of six liquid segments, each of which had a volume of 28 μl. Magnetic particles (1.4 μl of the magnetic particle reagent used in the TECHNICON IMMUNO 1 system were aspirated into the first segment (MP), with the remainder of fluid being particle wash buffer (25 mM Tris, pH 7.5, containing 0.2M NaCl, 0.1% Triton X-100 and preservative). R1 (10.4 μl of serum-based solution containing fluorescein-labeled antibody to TSH), R2 (10.4 μl of serum-based solution containing antibody to TSH conjugated with ALP) and S (7.2 μl of serum sample) were aspirated into the second segment. The next two segments (W1 and W2) were comprised of the same wash buffer used above in the MP segment. The fifth segment was R3, of the composition described above, with the key elements being the luminogenic substrate and the luminescence enhancer. The sixth segment was an inter-test buffer (same as the particle buffer described above), which was used to isolate adjacent tests. Magnetic transfers are depicted by the arrows in the FIG. 1. These transfers were facilitated by one of two magnetic transfer assemblies (M1 or M2). After an incubation of 13 minutes, during which sandwich formation occurred, M1 transferred the magnetic particles into the R1+R2+S segment to initiate capture. After an additional period of 6 minutes, M2 transferred the particles into the first wash segment. After an additional period of 12 seconds, M2 transferred the particles into the second wash segment. After another period of 12 seconds, M2 transferred the particles into the R3 segment, and light emission from this segment was detected as the stream of aqueous segments passed back and forth through the luminometer readhead.

Figure 2:
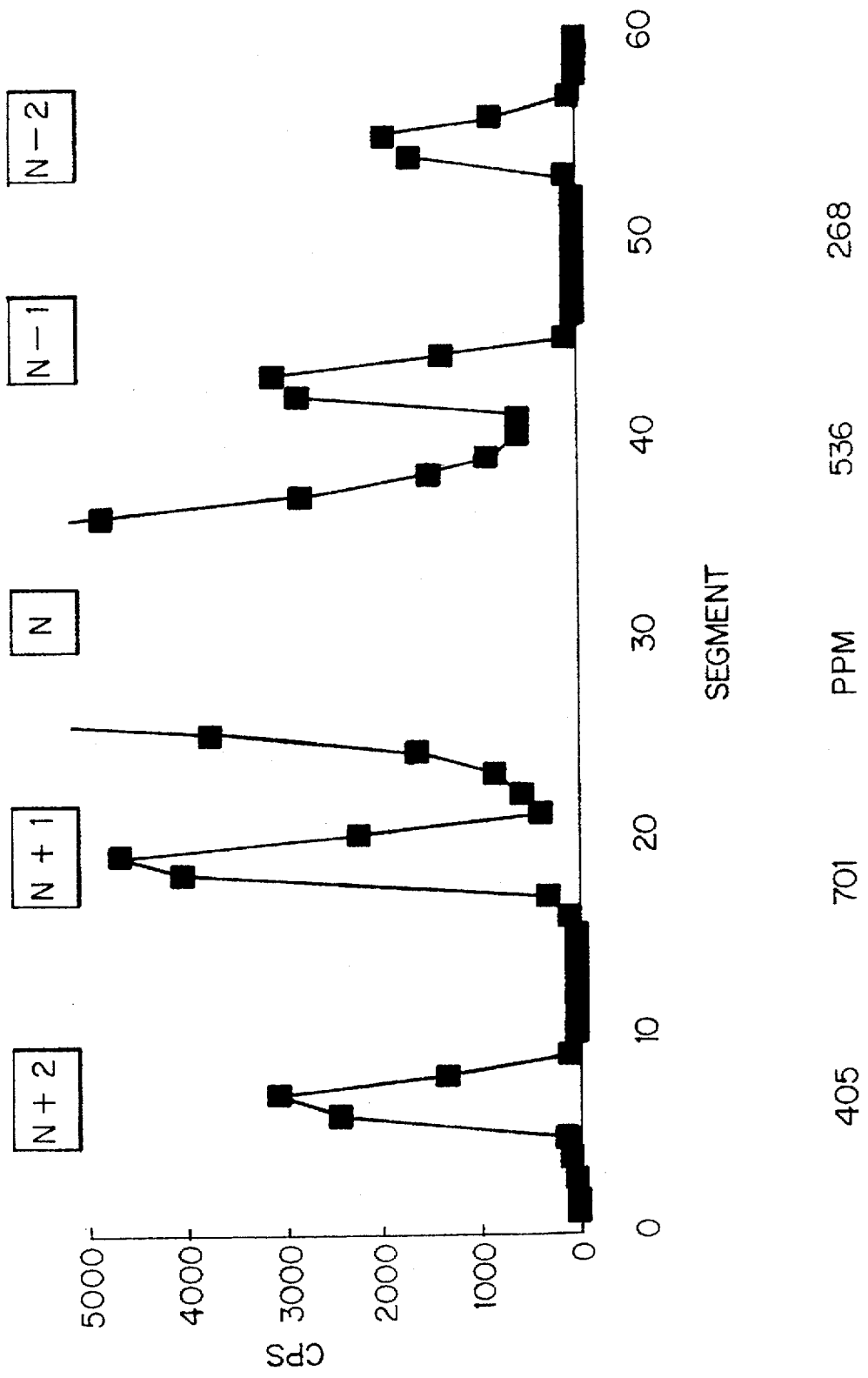
FIG. 2 is a profile of adjacent segments in the capsule chemistry analysis system showing the observed luminescence attributed to carryover as more fully described in the Examples below.

Since the Teflon tube is transparent to light, a problem with light piping (or "optical carryover") was expected. Specifically, some of the photons emitted from the R3 segment of an adjacent test could enter the Teflon material, propagate down the length of the tube and be scattered into the detector during the measurement of the signal of the test of interest. However, while a signal was detected in the adjacent tests, it did not occur in the expected manner. Instead of declining rapidly with distance from test N, peaks of light output were observed centered around the R3 segments of the adjacent test packages, as shown in FIG. 2 of the drawings. In FIG. 2, test N produced a high level of luminescence, approximately 7.5 million counts per seconds (cps). Tests N−1 and N−2 were aspirated into the tube before test N and preceded this test through the luminometer, and tests N+1 and N+2 followed after test N. The analysis system recorded photons counted for each individual air and liquid segment in the stream. The profile in FIG. 2 represents the average of 10 replicate panels of 5 tests each corrected for background luminescence signal produced in the absence of ALP. The reagent blank values subtracted from each data point were an average obtained from 10 replicate panels of 5 tests each. The magnitude of the carryover signal was computed by dividing the peak cps in each adjacent test by the peak cps in test N, expressed in parts per million (ppm).

Another possible explanation for this behavior was physical carryover of ALP from test N into the neighboring tests in an unintended manner. This could happen, for example, if the tube contained particulate materials deposited on the walls, which could disrupt the smooth motion of the liquid segments through the tube. However, placement of 10 mM inorganic phosphate in the R3 segments of the adjacent tests had no effect on the magnitude of the signals in the adjacent tests. Since this amount of phosphate would have inhibited ALP by at least 90% under these test conditions, the possibility of physical carryover was ruled out.

Figure 3:
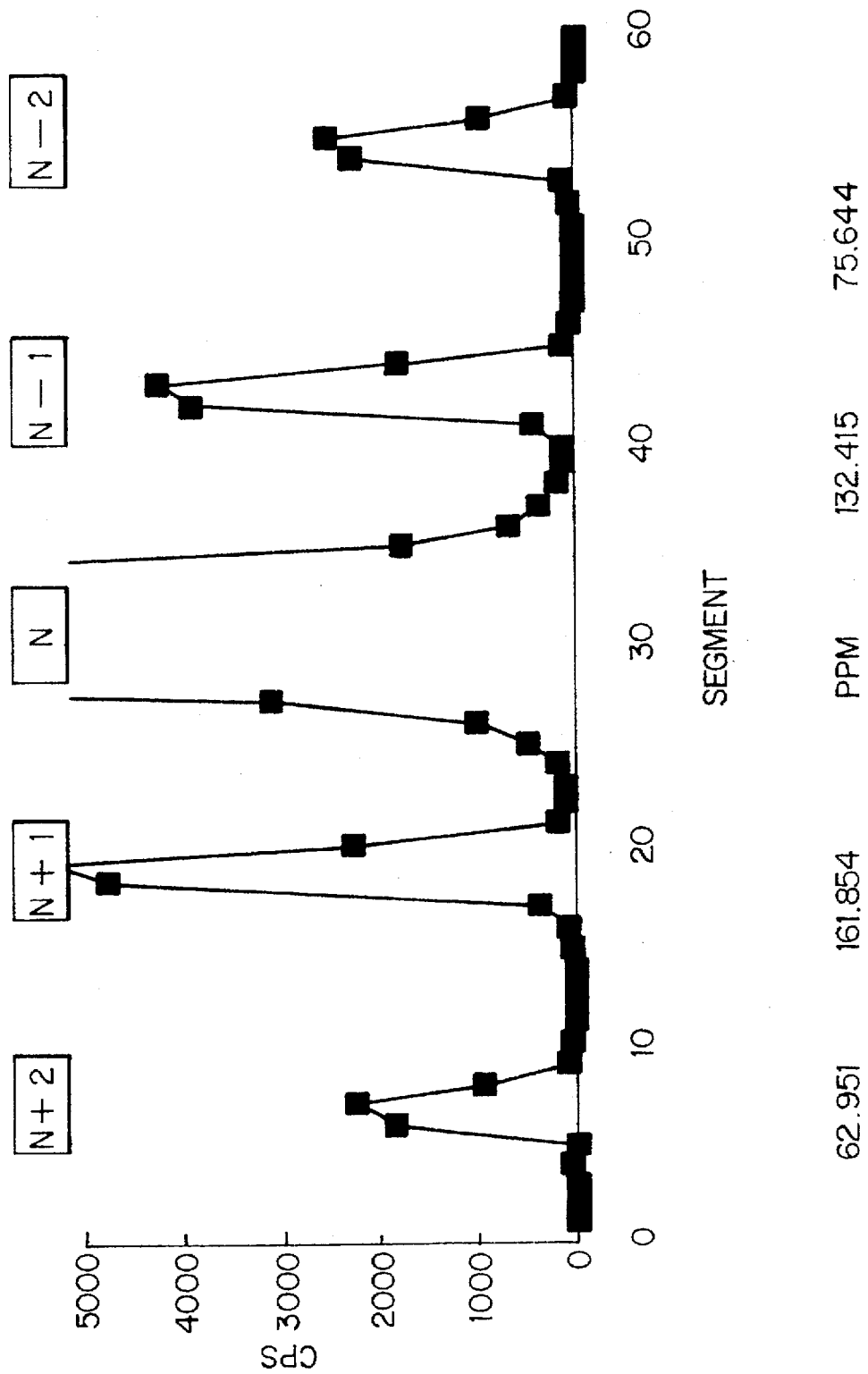
FIG. 3 is a further profile of adjacent segments observed in the experiments which are more fully described in the Examples below and which established that the carryover was not optical in nature.

To further rule out optical carryover, the fluorescent enhancer pyranine was omitted from test N only, but present in the adjacent tests. As a result, the magnitude of the signal in test N was lower by a factor of approximately 10. However, as shown in FIG. 3 of the drawings, the height of the peaks in the adjacent tests did not change significantly. The fact that the carryover signal did not change in the adjacent tests proportionately clearly demonstrated that this carryover was not optical.

Figure 4:
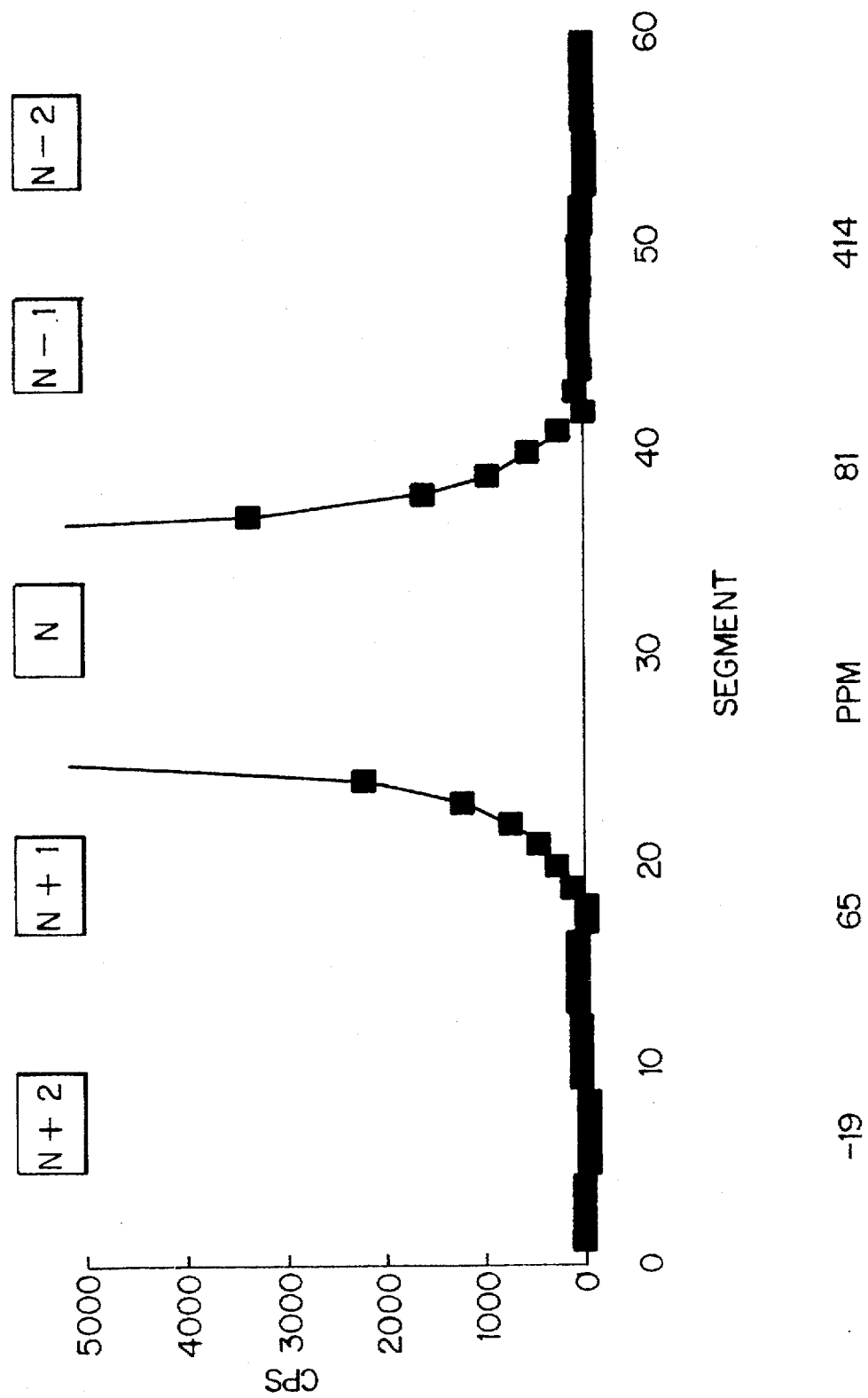
FIG. 4 is a further profile of adjacent segments observed in the experiments which are more fully described in the Examples below and which established that the carryover was in fact chemical in nature.

An additional and unexpected type of carryover was the cause of the carryover problem. It was found that the hydroxy dioxetane intermediate was sufficiently soluble in the fluorocarbon oil used to coat the inner wall of the Teflon tube, such that the carryover was due to transfer of dissolved hydroxy dioxetane intermediate via the oil into the R3 segments of the neighboring tests. This process was tested by changing the buffer of the R$_3$ segments in the adjacent tests from 1M DEA at pH 10 to 1M Tris at pH 7. At pH 7, dissolved hydroxy dioxetane intermediate in these R3 segments is stable and does not emit light. As shown in FIG. 4 of the drawings, this change in pH resulted in the complete elimination of the side bands of luminescence. The residual minor carryover in the N+1 and N−1 tests was due to the anticipated optical carryover. These results verified that the source of light emission in the peaks in the neighboring tests was "chemical carryover" of the hydroxy dioxetane derived from CSPD into the R3 segments of adjacent tests.

Example 7

Elimination of Observed Chemical Carryover with Dicarboxylic Acid-substituted Dioxetane 1

Table 1 shows the effect of using three other dioxetanes on the chemical carryover of the reaction intermediate. LUMIGEN PPD [4-(methoxy)-4-(3-phosphoryloxyphenyl)]spiro[1,2-dioxetane-3,2'-tricyclo[3.3.1.1$^{3,7}$]-decane], (Lumigen, Inc., Southfield, Mich., USA), dioxetane 2, a monocarboxylic acid derivative and dioxetane 1, a dicarboxylic acid derivative were each used in test formulations at the same concentration. The ppm column is the signal for the N+1 test, which represents worst case behavior. The carryover of the unmodified parent compound, PPD, was found to be more than twice as high as that observed with CSPD. Surprisingly, the monocarboxylic acid derivative, dioxetane 3, showed a reduction of only 84% in the magnitude of the chemical carryover. This indicated that a single charged group was insufficient to completely prevent solubilization of the reaction intermediate in the fluorocarbon oil. However, the dicarboxylic acid derivative was 100% effective, indicating that two charged groups were fully adequate to achieve the desired behavior.

TABLE 1

Reduction of Chemical Carryover

| Compound | ppm | % Reduction |
| --- | --- | --- |
| LUMIGEN PPD | 1640 | |
| Dioxetane 2 | 260 | 84 |
| Dioxetane 1 | 0 | 100 |

Example 8

The Role of Enhancers

As part of the optimization of a reagent based on dioxetane 1, a number of enhancer materials was examined. At pH 9.6, Enhancer A (1-trioctylphosphoniummethyl-4-tributylphosphoniummethylbenzene dichloride) increased the luminescent signal by a factor of 6.2, and Enhancer B (poly(vinylbenzyltributylphosphonium chloride)) increased the signal by a factor of 19.7. At pH 10.0, Enhancer A increased the signal by a factor of 4.8, and Enhancer B increased the signal by a factor of 18.9.

Despite the fact that Enhancer B achieved higher light intensities, Enhancer A was preferred for use on the analysis system since it is a low molecular weight monomeric compound. Polymeric compounds, especially if they are polycationic, interact with serum components, causing precipitation, which would pose significant problems for the operation of the analysis system.

Both fluorescein and pyranine were found to be effective as supplementary fluorescers in combination with Enhancer A. Alone, these fluorescers must be used at relatively high concentrations (3 mM) in order to achieve an enhancement of about ten-fold. However, in combination with Enhancer A, a synergistic effect was observed, in which a comparable enhancement resulted at 100-fold lower concentrations of fluorescer than needed in the absence of the enhancer. Tables 2 and 3 show the extent of enhancement by pyranine and fluorescein, respectively, in the presence of 1 mg/ml of Enhancer A.

TABLE 2

Enhancement by Pyranine with Enhancer A

| [Pyranine] (mM) | Enhancement Factor |
| --- | --- |
| 0.01 | 3.7 |
| 0.02 | 7.3 |
| 0.03 | 9.8 |
| 0.04 | 12.2 |
| 0.05 | 13.7 |

TABLE 3

Enhancement by Fluorescein with Enhancer A

| [Fluorescein] (mM) | Enhancement Factor |
| --- | --- |
| 0.01 | 2.6 |
| 0.02 | 4.0 |
| 0.05 | 7.1 |
| 0.10 | 8.7 |

Example 9

Optimized Formulation for Capsule Chemistry Analysis System

The above described observations have led to the development of an optimized formulation for the capsule chemistry analysis system. This formulation is comprised of 0.1–1 mM dioxetane 1, 0–0.05 mM pyranine, 0.1–5 mg/mL Enhancer A, 0–1 mM $Mg^{+2}$, 0.1–1M 2-amino-2-methyl-1-propanol (pH 10.0) and 0.01–1% Triton X-100. Use of this formulation results in complete elimination of the chemical carryover problem and enhanced performance.

Example 10

Stability of 1, 3, 4 and 5 Measured by Enzyme Assay

Figure 5:
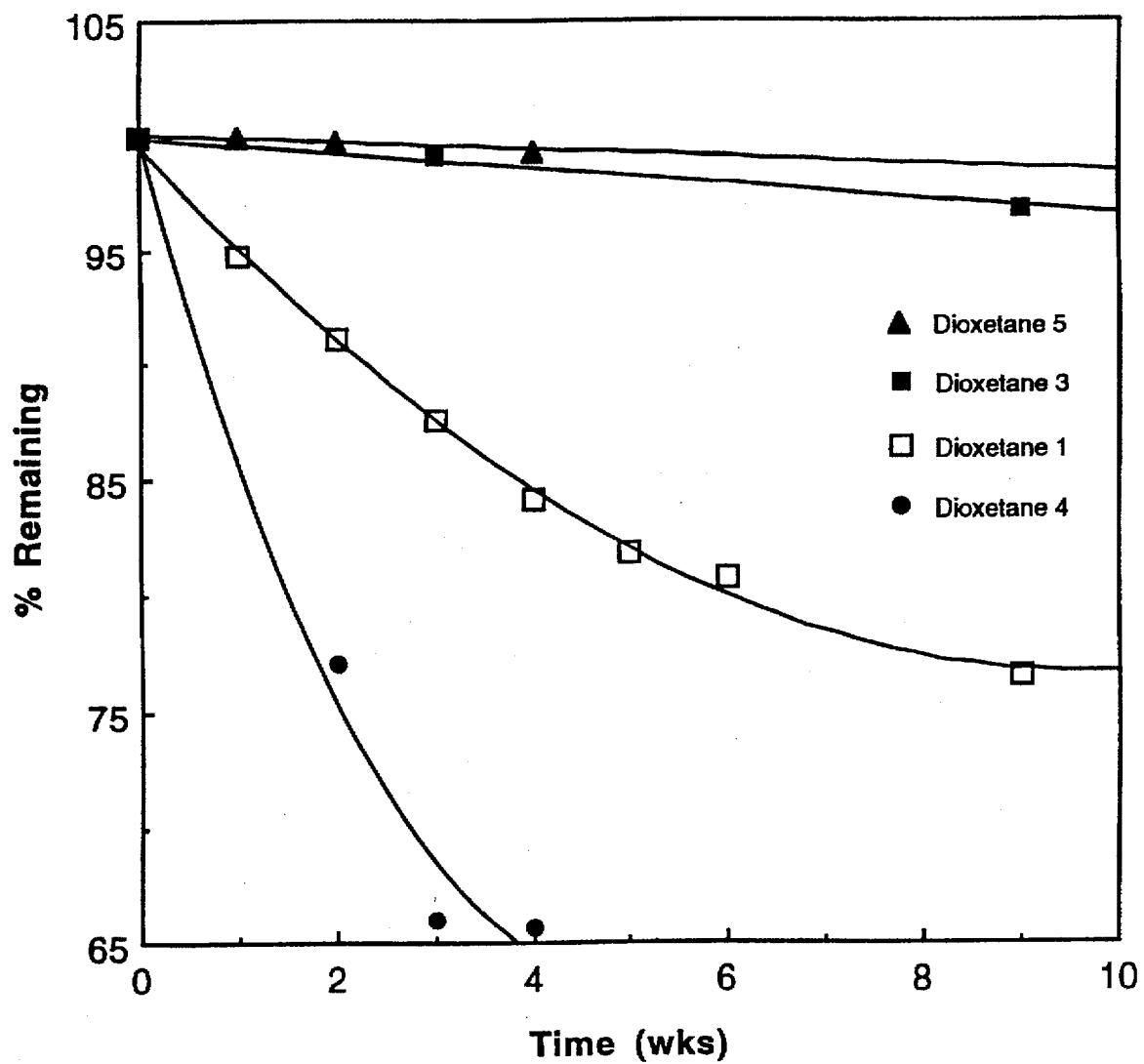
FIG. 5 is a graph depicting the relative rates of decomposition at 25° C. of a fluoro-substituted dioxetane, a chloro-substituted dioxetane, a methyl-substituted dioxetane and a reference dioxetane containing no halogen atoms.

Formulations comprising 0.1 mg/mL Enhancer A, 0.88 mM $Mg^{+2}$, 0.2M 2-amino-2-methyl-1-propanol, pH 10, 0.1% Triton X-100 and 0.5 mM dioxetane 1, 3, 4 and 5, respectively, were prepared and stored in opaque polyethylene bottles at 4° C., 25° C. and 40° C. Twenty four 100 μL aliquots from each bottle were pipetted into the wells of a 96 well plate and the solutions incubated at 37° C. Into each well 10 μL solutions containing $8 \times 10^{-17}$ moles of AP were injected and light intensity integrated over five hours. Data are the average of all 24 wells. The experiment was repeated at the indicated time intervals for each dioxetane. The results in FIG. 5 show the comparative stability of the three formulations at 25° C. As shown in FIG. 5, fluoro-substituted dioxetane 3 was found to exhibit substantially better storage stability than chloro-substituted dioxetane 4 and the non-halo-substituted dioxetane 1. Dioxetanes 3 and 5 were also substantially more stable than 1 or 4 at 40° C.

TABLE 4

Storage Stability of Formulations

| Time (wks) | % of Dioxetane Remaining | | | |
|---|---|---|---|---|
| | 1 | 3 | 4 | 5 |
| 0 | 100 | 100 | 100 | 100 |
| 1 | 94.8 | | | 100 |
| 2 | 91.1 | | 77.0 | 99.8 |
| 3 | 87.5 | 99.1 | 66.0 | |
| 4 | 84.1 | | 65.6 | 99.4 |
| 5 | 81.8 | | | |
| 6 | 80.7 | | | |
| 9 | 76.5 | 96.9 | | |
| 10 | | | 57.5 | |
| 12 | | 96.7 | | |
| 14 | | 93.8 | | |
| 21 | | 93.6 | | |

Example 11

Performance of 3

A detection reagent incorporating dioxetane 3 was evaluated in a test system as described in Example 6. The test material was a fluorescein-labeled alkaline phosphatase conjugate which was captured onto the magnetic particles. Assays for AP using the reagent containing 3 produced results with sensitivity, dynamic range and precision comparable to the results using dioxetane 1.

The foregoing examples are illustrative only and not intended to be restrictive. The scope of the invention is indicated only by the appended claims and equivalents.

What is claimed is:

1. A dioxetane of the formula:

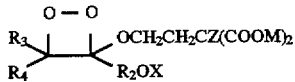

having increased storage stability wherein $R_3$ and $R_4$ are each selected from the group consisting of acyclic, cyclic and polycyclic organic groups which can optionally be substituted with heteroatoms and which can optionally be joined together to form a cyclic or polycyclic ring group spiro-fused to the dioxetane ring, wherein $R_2$ is an aryl ring group selected from the group consisting of phenyl and naphthyl groups which can include additional substituents, wherein Z is selected from the group consisting of a fluorine atom and an alkyl group of 1–4 carbons, M is selected from hydrogen, an alkali metal ion or a quaternary ammonium or phosphonium ion and wherein X is a protecting group which can be removed by an activating agent to produce light.

2. A dioxetane of the formula:

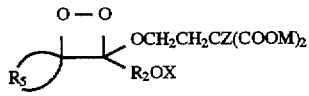

having increased storage stability wherein $R_5$ is selected from the group consisting of cyclic and polycyclic alkyl groups which are spiro-fused to the dioxetane ring and which contain 6 to 30 carbon atoms and which can optionally include additional substituents, wherein $R_2$ is an aryl ring group selected from the group consisting of phenyl and naphthyl groups which can optionally include additional substituents, wherein Z is selected from the group consisting of a fluorine atom and an alkyl group of 1–4 carbons, wherein M is selected from hydrogen, an alkali metal ion or a quaternary ammonium or phosphonium ion and wherein X is a protecting group which can be removed by an activating agent to produce light.

3. The dioxetane of claim 2 having the formula:

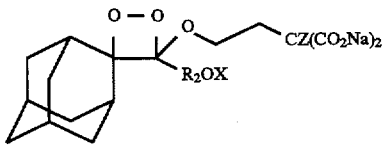

4. The dioxetane of any one of claims 1, 2 or 3 wherein the OX group is selected from the group consisting of an $O^-M^+$ group wherein M is selected from the group consisting of hydrogen, an alkali metal ion, a quaternary ammonium and a quaternary phosphonium ion, an $OOCR_8$ group wherein $R_8$ is selected from the group consisting of alkyl and aryl groups containing 2 to 8 carbon atoms and optionally containing heteroatoms, $OPO_3^{-2}$ salt, $OSO_3^-$ salt, β-D-galactosidoxy and β-D-glucuronidyloxy groups.

5. A dioxetane of the formula:

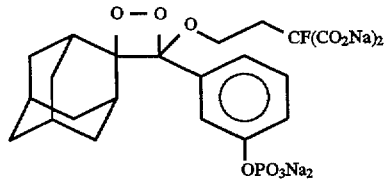

which has increased storage stability.

6. A dioxetane of the formula:

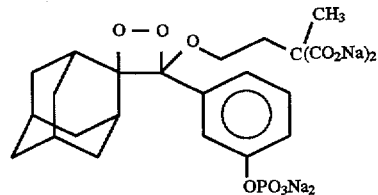

which has increased storage stability.

* * * * *